US007138419B2

(12) United States Patent
Montgomery et al.

(10) Patent No.: US 7,138,419 B2
(45) Date of Patent: *Nov. 21, 2006

(54) PROCESS FOR MANUFACTURING BULK SOLUTIONS AND A LYOPHILIZED PURE α-AZTREONAM LYSINATE

(75) Inventors: Alan Bruce Montgomery, Medina, WA (US); Iain Duncan, Seattle, WA (US); Peter Carbonaro, Sammanish, WA (US)

(73) Assignee: Corus Pharma, Inc., Seattle, WA (US)

( * ) Notice: Subject to any disclaimer, the term of this patent is extended or adjusted under 35 U.S.C. 154(b) by 51 days.

This patent is subject to a terminal disclaimer.

(21) Appl. No.: 10/882,985

(22) Filed: Jun. 30, 2004

(65) Prior Publication Data

US 2005/0063912 A1 Mar. 24, 2005

Related U.S. Application Data

(63) Continuation-in-part of application No. 10/613,639, filed on Jul. 3, 2003, which is a continuation-in-part of application No. 10/027,113, filed on Dec. 20, 2001, now Pat. No. 6,660,249.

(60) Provisional application No. 60/258,423, filed on Dec. 27, 2000.

(51) Int. Cl.
*A01N 33/10* (2006.01)
*A01N 33/16* (2006.01)
*A01N 33/24* (2006.01)
*A01N 43/78* (2006.01)

(52) U.S. Cl. .......................... 514/365; 514/2; 514/640
(58) Field of Classification Search .............. 514/640, 514/365, 563, 601, 2
See application file for complete search history.

(56) References Cited

U.S. PATENT DOCUMENTS

| | | | |
|---|---|---|---|
| 4,550,105 A | 10/1985 | Matsuo et al. | 514/210 |
| 4,572,801 A | 2/1986 | Matsuo et al. | 260/245.4 |
| 4,610,824 A | 9/1986 | Trüner | 540/335 |
| 4,673,739 A | 6/1987 | Matsuo et al. | 540/355 |
| 4,775,670 A | 10/1988 | Sykes et al. | 514/210 |
| 4,822,788 A | 4/1989 | Kishimoto et al. | 514/210 |
| 4,826,973 A | 5/1989 | Anderson et al. | 540/335 |
| 4,888,998 A | 12/1989 | Buzza et al. | 73/864.21 |
| 4,946,838 A | 8/1990 | Floyd et al. | 514/210 |
| 5,875,776 A | 3/1999 | Vaghefi | 128/203.15 |
| 5,994,340 A | 11/1999 | Maiti et al. | 514/192 |
| 6,054,431 A | 4/2000 | Horwitz et al. | 514/12 |
| 6,518,239 B1 | 2/2003 | Kuo et al. | 514/2 |
| 2004/0009126 A1 | 1/2004 | Pilkiewicz et al. | 424/46 |

FOREIGN PATENT DOCUMENTS

EP 0297580 A1 1/1989 ............ 417/12

OTHER PUBLICATIONS

Bastin, R. J. et al. "Salt Selection and Optimisation Procedures for Pharmaceutical New Chemical Entities" Org. Proc. Res. & Develop. 2000, 4, 427-435.*
The Dictionary of Modern Medicine, J.C. Segen, Ed. Parthenon Publishing Group: New Jersey, 1992, p. 517-518.*
Brian E. Scully, M. B., et al., Use of Aztreonam in the Treatment of Serious Infections Due to Multiresistant Gram-Negative Organisms, Including *Pseudomonas Aeruginosa*, *The American Journal of Medicine*, 78:251-261 (Feb. 1985).
John A. Bosso, et al., Efficacy of Aztreonam in Pulmonary Exacerbations of Cystic Fibrosis, *The Pediatr. Infect. Dis. J.*, 6:393-397 (1987).
James L. Cook, M. D., Gram-Negative Bacillary Pneumonia in the Nosocomial Setting, *The American Journal of Medicine*, 88:3C-34S-37S.
A. Boccazzi, et al., The Pharmacokinetics of Aztreonam and Penetration into the Bronchial Secretions of Critically Ill Patients, *Journal of Antimicrobial Chemotherapy*, 23:401-407, (1989).
Harold C. Neu, M. D., Aztreonam Activity, Pharmacology and Clinical Uses, The American Journal of Medicine, 88:3C-2S-3C-6S.
Stephen C. Aronoff, et al., *In Vitro* Activities of Aztreonam, Piperacillin, and Ticarcillin Combined with Amikacin Against Amikacin Resistant *Pseudomonas aruginosa* and *P. cepacia* Isolates from Children with Cystic Fibrosis, *Antimicrobial Agents and Chemotherapy*, 25/2:279-280 (Feb. 1984).
John M. Matsen, et al., The Use of Aztreonam in the Cystic Fibrosis Patient, *Pediatr. Infect. Dis. J.*, 8/9:S117-S119 (1989).
Lisa Saiman, MD, Antimicrobial Resistance Among *Burkholderia, Stentrophomonas* and Alcaligenes Isolates Studied by the CF Eferal Center for Susceptibility and Synergy Testing, 1988 Cystic Fibrosis Conference, Symposium Session Summaries, 118-119 (1998).
Preston W. Campbell III, MD., et al., Use of Aerosolized Antibiotics in Patients with Cystic Fibrosis, Consensus Conference, pp. 775-789 (Sep. 1999).
Klaus Florey, Aztreonam, *Analytical Profiles of Drug Substances*, 17:1-39 (1988).
Ajit B. Thakur, et al., Interaction of Metronidazole with Antibiotics Containing the 2-Aminothiazole Moiety, *Pharmaceutical Research*, 8/11:1424-1429 (1991).
S. A. Ranadive, et al., Formation, Isolation and Identification of Oligomers of Aztreonam, *European Journal of Pharmaceutical Sciences*, 3:281-291 (1995).
Hiram C. Polk, Jr. MD, et al., Treatment of Pneumonia in Mechanically Ventilated Trauma Patients, *Arch Surg.*, 132:1086-1092 (Oct. 1997).
Stephen P. Newman, Ph.D., Aerosol Deposition Considerations in Inhalation Therapy, *Chest.* 88:2, 152S-160S (Aug. 1995).

(Continued)

*Primary Examiner*—Johann R. Richter
*Assistant Examiner*—James H. Alstrum-Acevedo
(74) *Attorney, Agent, or Firm*—Hana Verny; Peters, Verny, Jones, Schmitt & Aston LLP

(57) ABSTRACT

A process for manufacturing bulk solutions and lyophilized pure α-aztreonam lysinate for large scale production of an inhalable aztreonam is disclosed, as is a pure α-aztreonam lysinate for inhalation. A dry powder or lyophilized pure α-aztreonam lysinate composition for inhalation is also disclosed.

19 Claims, 6 Drawing Sheets

OTHER PUBLICATIONS

Gerald C. Smaldone, et al., Aerosolized Antibiotics: Current and Future, *Respiratory Care*, 45/6:667-675 (Jun. 2000).

Thomas G. O'Riordan, MD, Inhaled Antimicrobial Therapy: From Cystic Fibrosis to the Flue, *Respiratory Care*, 45/7:836-845 (Jul. 2000).

Robert G. Bell, et al, Stability of Intravenous Admixtures of Aztreonam and Cefoxitin, Gentamicin, Metronidazole, or Tobramycin, *American Journal of Hospital Pharmacy*, 43:1444-1453 (Jun. 1986).

Michael J. James, et al., Stability of Intravenous Admixtures of Aztreonam and Ampicillin, *American Journal of Hospital Pharmacy*, 42:1095-1100 (May 1985).

Woo, M.S., et al., Use of Aerosolized Aztreonam in CF Lung Transplant Patients Colonized With *Burkholderia cepacia*, 2002 Cystic Fibrosis Conference, 322/419 ★.

Petra Borsje, MD, et al., Aerosol Therapy in Cystic Fibrosis: A Survey of 54 CF Centers, *Pediatric Pulmonology*, 30:368-376 (2000).

Rafael Cantón, PD, PhD, Lung Colonization With *Enterobacteriaceae* Producing Extended-Spectrum β-Lactamases in Cystic Fibrosis Patients, *Pediatric Pulmonology*, 24:213-217 (1997).

S. Ballestero, et al., *Stenotophomonas maltophilia* in Cystic Fibrosis Patients, 20th European Cystic Fibrosis Conference, Brussels, Belgium (Jun. 18-21, 1995).

Sira Carrasco, et al., The General Approach to Cystic Fibrosis Pulmonary Infection in Spain, *Cystic Fibrosis Pulmonary Infections: Lessons From Around The World*, Chapter 18, pp. 223-230 (1996).

Desppina Daisy Frangolias, et al., *Burkholderia cepacia* in Cystic Fibrosis, *Am J of Respir Crit Care Med*, 160:1572-1577 (1999).

John J. LiPuma, MD, *Burkholderia cepacia*, Management Issues and New Insights, *Clinics in Chest Medicine*, 19/3:473-486 (Sep. 1998).

Diane H. Johnson, MD, et al., Aztreonam, *Medical Clinics of North America*, 79/4:733-743 (Jul. 1995).

Dapena Fernandez J., et al., Inhaled Aztreonam Therapy in Patients With Cystic Fibrosis Colonized With *Pseudomonas aeruginosa*, *Spanish Annals on Pediatrics*, 40/3 (1994).

John A. Bosso, et al., *In Vitro* Activities of Combinations of Aztreonam, Ciprofloxacin, and Ceftazidme against Clinical Isolates of *Pseudomonas aeruginosa* and *Pseudomonas cepacia* from Patients with Cystic Fibrosis, *Antimicrobial Agents and Chemotherapy*, 34/3:487-488 (Mar. 1990).

* cited by examiner

□ API
▨ BULK SOLUTION α-AZTREONAM
▨ LYOPHILIZATE α-AZTREONAM
MANUFACTURING PROCESS II.

PROCESS FOR MANUFACTURING BULK SOLUTIONS AND A LYOPHILIZED PURE α-AZTREONAM LYSINATE

This application is a continuation-in-part of U.S. application Ser. No. 10/613,639, filed on Jul. 3, 2003 which is a continuation-in-part of U.S. application Ser. No. 10/027,113 filed on Dec. 20, 2001, issued as the U.S. Pat. No. 6,660,249 on Dec. 9, 2003, which is based on and claims priority of the Provisional application Ser. No. 60/258,423, filed on Dec. 27, 2000.

BACKGROUND OF THE INVENTION

1. Field of the Invention

The current invention concerns a process for manufacturing bulk solutions and lyophilized pure α-aztreonam lysinate for preparation of inhalable formulations for treatment of pulmonary bacterial infections caused by gram negative bacteria. In particular, the invention concerns a manufacturing process for preparation of pure α-aztreonam lysinate without need for conversion to β-aztreonam. The process is fast, safe, practical and economical.

The pure α-aztreonam lysinate bulk solution is easily converted into a lyophilized form. The lyophilized α-aztreonam lysinate is delivered to the lung as an aerosol or as an inhalable dry powder. For aerosolization, about 75 mg/ml of lyophilized α-aztreonam lysinate is reconstituted in about 1 to about 5 ml of normal or diluted saline or another aqueous solution of pH between 4.5 and 7.5, delivered to the lung endobronchial space in an aerosol having mass medium average diameter particles predominantly between 1 to 5μ using a nebulizer able to atomize the α-aztreonam lysinate solution into particles of required sizes.

For delivery of dry inhalable powder, α-aztreonam lysinate is lyophilized, milled or spray dried to particle sizes between about 1 and 5μ. Both the dry powder formulation or a reconstituted lyophilized α-aztreonam lysinate solid for aerosolization have a long shelf-life and storage stability.

2. Background and Related Disclosures

A wide variety of gram-negative bacteria cause severe pulmonary infections. Many of these bacteria are or become resistant to commonly used or specialty antibiotics and require treatment with new types of antibiotics.

Aztreonam is a synthetic antibiotic which has a good biological activity against gram-negative bacteria and its arginine salt derived from the β-aztreonam has previously been used for intravenous treatment of bacterial infections. However, its use is severely limited due to its low efficacy requiring administration of very large intravenous doses ranging from 1000 to 4000 mg a day.

Aztreonam is currently commercially available only as an arginine salt. Arginine has been shown to be toxic to the lung and causes lung tissue irritation, inflammation, bronchospasm and cough and therefore is not suitable for a delivery by aerosolization. Consequently, aztreonam arginine salt is not approved for inhalation use in the United States or elsewhere. Moreover, the β-aztreonam form used for preparation of aztreonam arginine is not stable and requires special handling conditions. Thus, although aztreonam would be an antibiotic of choice for complementary treatment of patients treated with tobramycin or other antibiotics, such treatment is not practical because of the high doses required and complications encountered with the β-aztreonam arginine salt.

However, aztreonam could become a drug of choice for inhalation treatment, if it could be prepared as a different salt than arginine, if such salt would be suitable for inhalation and if the aztreonam form would permit manufacturing of bulk solutions and salt conversion without raising the impurity levels.

Suitability of aztreonam for treatment of gram-negative bacterial infections by inhalation is disclosed in the U.S. Pat. No. 6,660,249 issued on Dec. 9, 2003 and the preferable aztreonam salt, namely α-aztreonam lysinate, even better suited for such purposes, is disclosed in a co-pending patent application Ser. No. 10/613,639, filed on Jul. 3, 2003, both by inventors. Both the U.S. Pat. No. 6,660,249 and the patent application Ser. No. 10,613,639 are hereby incorporated by reference in their entirety.

Thus it would be advantageous and desirable to provide a pure aztreonam salt which would be easier to manufacture and handle when an inhalable aztreonam formulation for delivery of aztreonam by aerosol or a dry powder is prepared.

It is, therefore, a primary object of this invention to provide a manufacturing process for preparation of a pure α-aztreonam lysinate without need for conversion of aztreonam into β-aztreonam, said pure α-aztreonam lysinate being suitable for delivery of aztreonam by inhalation into lungs for treatment of pulmonary gram-negative infections.

All patents, patent applications and publications cited herein are hereby incorporated by reference.

SUMMARY

One aspect of the current invention is a manufacturing process for preparation of a pure α-aztreonam lysinate.

Still another aspect of the current invention is a process for preparation of a bulk solution or a lyophilized pure α-aztreonam lysinate.

Yet another aspect of the current invention is a process of preparation of a bulk solution of α-aztreonam lysinate comprising about 75 mg of aztreonam per 1 ml of solvent.

Another aspect of the current invention is a manufacturing process for preparation of α-aztreonam lysinate without need for conversion of α-aztreonam to β-aztreonam.

Still another aspect of this invention is a process for preparation of α-aztreonam lysinate from α-aztreonate wherein the resulting α-aztreonam lysinate has a better stability, higher purity and better yield.

Another aspect of this invention is a two-part reconstitution system comprising an α-aztreonam lysinate in dry or lyophilized powder form and a diluent stored separately until use.

DEFINITIONS

Figure 1:
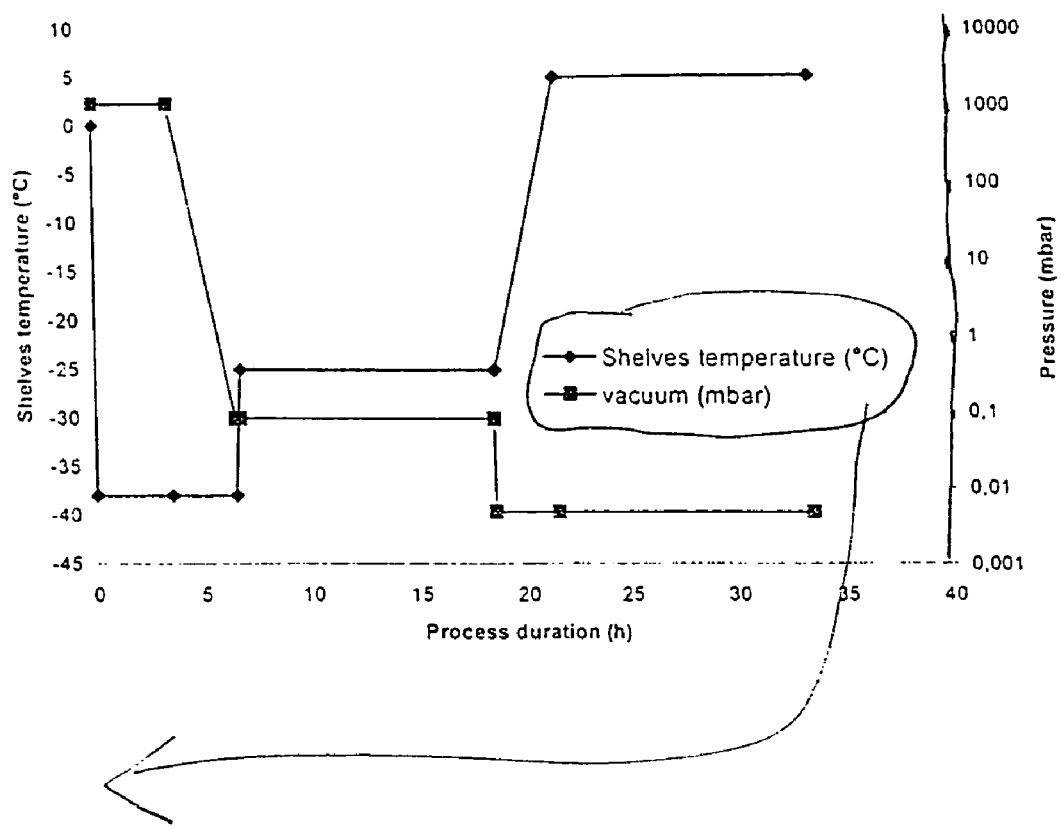
FIG. 1 is a scheme illustrating lyophilization-parameters used for manufacturing a lyophilized α-aztreonam lysinate.

As used herein:

"Alpha form of aztreonam" or "α-aztreonam" means an alpha stereochemical configuration of aztreonam. The alpha form of aztreonam is distinguishable from the beta, gamma and delta forms of aztreonam. Each form has different chemical and physical properties, such as, for example, stability, crystallization point and diffraction curve. Differences between the α- and β-aztreonam forms are described, for example in U.S. Pat. No. 4,946,838, incorporated by reference. Alpha and beta aztreonam arginine salt are described in EP application 0 297 580 B1, incorporated by reference. Alpha, beta, gamma and delta forms of aztreonam and their chemical and physical properties are described in U.S. Pat. No. 4,826,973, incorporated by reference. All the above cited patents are herein incorporated by reference in their entirety.

"α-Aztreonam lysinate composition" or "α-aztreonam lysinate formulation" means a composition or formulation comprising an indicated amount of aztreonam lysinate salt. Thus if, for example, the dose of aztreonam lysinate comprises one molar amount of aztreonam free base it contains 1.8 molar amount of lysine. Typically, said α-aztreonam lysinate mixture comprises from about 50 mg to about 300 mg of anhydrous α-aztreonam and from about 70 mg to about 420 mg of lysine monohydrate per one milliliter of water for injection.

"Concentrated α-aztreonam lysinate" means the α-aztreonam lysinate concentrated into a form which permits dilution of, or more than, 75 mg of α-aztreonam lysinate in 1 ml of diluent.

"Lyophilizate" means a dry residuum of α-aztreonam lysinate obtained by a process of lyophilization from a α-aztreonam lysinate bulk solution.

"Normal saline" means water solution containing 0.9% (w/v) NaCl.

"Diluted saline" means normal saline containing 0.9% (w/v) NaCl diluted into its lesser strength from about 0.1% to about 0.8%.

"Half normal saline" or "½ NS" means normal saline diluted to its half strength containing 0.45% (w/v) NaCl.

"Quarter normal saline" or "¼ NS" means normal saline diluted to its quarter strength containing 0.225% (w/v) NaCl.

"One tenth normal saline" or "1/10 NS" means normal saline diluted to its one tenth strength containing 0.09% (w/v) NaCl.

"Substantially" means at least 90% but preferably 95%.

"Predominantly" means including at least 70% but preferably 90%.

"Physiologically acceptable solution" means a saline diluted to between 1/10 NS or 1 NS or another aqueous solution comprising from about 31 to about 154 mM of chloride.

"Composition" means a formulation containing α-aztreonam lysinate and additionally containing other components, such as excipients, diluents, isotonic solutions, buffers, etc.

"Formulation" means a specific composition formulated for specific use, such as for aerosolization of aztreonam lysinate containing solution or nebulization of dry powder.

DETAILED DESCRIPTION OF THE INVENTION

The current invention concerns a process for manufacturing bulk solutions as well as a lyophilized pure α-aztreonam lysinate from α-aztreonam without need for conversion of α-aztreonam into β-aztreonam.

The process for preparation of a pure and stable α-aztreonam lysinate is novel in that until now, the α-aztreonam was described as an unstable intermediate suitable only for preparation of a stable β-aztreonam and its conversion to β-aztreonam was required for preparation of therapeutically useful aztreonam arginine.

It has been now discovered that aztreonam lysinate derived from the α-aztreonam, as compared to the β-aztreonam, prepared according to the process of the invention results in a more pure product. Resulting α-aztreonam lysinate has better properties then β-aztreonam lysinate and is more suited for preparation of a lyophilized or dry powder aztreonam formulation for inhalation. The use of α-aztreonam form for preparation of the α-aztreonam lysinate provides demonstrable advantages in manufacturing processes of a lyophilized or dry powder product and results in the product with higher purity and better stability.

I. Aztreonam Generally

Aztreonam, known under its chemical name (Z)-2-[[[(2-amino-4-thiazolyl)[[(2S,3S)-2-methyl-4-oxo-1-sulfo-3-azetidinyl]carbamoyl]methylene]amino]oxy]-2-methylpropionic acid, is a free acid synthetic antibiotic having antibacterial activity against most gram-negative bacteria.

Aztreonam is a monobactam with a unique monocyclic beta-lactam nucleus that is structurally different from other β-lactam antibiotics, such as, for example, penicillins, cephalosporins, or cephamycins. The beta-lactam moiety of aztreonam is activated by a sulfonic acid substituent in the 1-position of the ring. An aminothiazolyl oxime side chain of aztreonam in the 3-position and a methyl group in the 4-position confer a specific antibacterial spectrum and beta-lactamase stability. Aztreonam is chemically known and available as alpha, beta, gamma and delta forms, each having different stability, crystallization point and diffraction curve.

Aztreonam arginine salt, known under its trade name AZACTAM® is derived from β-aztreonam and is commercially available from DURA Pharmaceuticals, Inc., San Diego, Calif. AZACTAM formulated as arginine salt is currently FDA approved only for intramuscular or intravenous use (*PDR*, pg. 1159 (2001)).

A. Disadvantages of Aztreonam Arginine Salt

Currently, the only commercially available aztreonam (AZACTAM) comprises arginine that has been found to cause pulmonary inflammation when administered in an aerosol form to the lung of the human patients. When used as a potential aerosolized mucolytic agent in cystic fibrosis patients, it caused the lung inflammation, bronchospasm and irritation. A study described in *Pediatrics,* 55:96–100 (1975) identifies arginine as a substrate for production of nitric oxide radicals and recommends that arginine should not be used for inhalation in patients. Consequently, because it is formulated as arginine salt, AZACTAM is not suitable or approved for inhalation.

Based on these observations, in order to provide a safe inhalable form of aztreonam, clearly, another aztreonam salt is needed for treatment of pulmonary infections by inhalation.

B. α- and β-Aztreonam

Previously, a preparation of aztreonam arginine and other salts, but not lysinate, involved almost exclusively the β-form of aztreonam. Alpha form of aztreonam was previously found to be unstable and unusable for preparation of therapeutic compositions. On the other hand, β-aztreonam was considered to be the stable form and if the α-aztreonam was used at all it was first converted to the β-aztreonam.

The U.S. Pat. No. 4,946,838 presents conclusive evidence that up-to-date α-aztreonam is considered to be an unstable form of aztreonam which must be converted to the β-aztreonam before it is used for preparation of any therapeutic product. The EPO application EP 0297580B1 describes preparation of aztreonam arginine and other salts derived from α- or β-aztrebnam. Salt disclosed therein are specifically limited to arginine and sodium containing salts, such as sodium carbonate, sodium bicarbonate, sodium citrate, sodium phosphate and sodium hydroxide. Specifically, the application identifies α- or β-aztreonam mixed with arginine or another above named salt in dry state and then mixed with water to bring the pH to 5.0. The application does not disclose the use of aztreonam for aerosol use or preparation of aztreonam as a lysine salt.

1. Stability of α- and β-Aztreonam

Aztreonam can exist either in anhydrous amorphous and crystalline forms or in hydrated and solvated crystalline forms. The amorphous and hydrated forms interconvert under certain temperature and humidity conditions, and are both unstable. In the solid state, the anhydrous crystalline and solvated forms show good stability without interconversion. However in the presence of excipients that release moisture, the anhydrous crystalline form rapidly decomposes to an extent dependent on moisture content and temperature.

Stability of the α- or β-aztreonam compound is determined by its loss at various temperatures. The prior art supports general belief that α-aztreonam is an unstable form of aztreonam. According to the prior art reports, after one week of storage, α-aztreonam shows approximately 1% loss at room temperature whereas at 80° C. loss reaches 80%. In contrast, β-aztreonam, after 12 month storage at temperature between −20° C. and 40° C., has less than 2% increase in impurity level and a decrease of only 3.0 to 3.5% in potency. Based on these results, β-aztreonam would seem to be a better and more stable compound.

However, α-aztreonam lysinate prepared according to the process of the invention was found to contain less impurities and have a better stability and is thus a more pure and stable compound.

2. Purity of α- and β-Aztreonams

For preparation of inhalable product, the active ingredient must be relatively pure or must be purified to remove impurities which do or would potentially cause bronchospasm, inflammation, irritation or cough. Consequently, the aztreonam for inhalation must be either prepared in a pure form or must be purified.

The type and degree of impurities in the inhalation formulation are important for and have a specific impact on the long term stability of the drug and on the shelf-life of the final product.

According to the prior art, the crystalline form of α-aztreonam is considered to be an unstable intermediary which must be converted to the stable β-aztreonam. Such conversion is achieved by recrystallization of α-aztreonam from an organic solvent, typically ethanol, into a very stable β-aztreonam. However, as a consequence of the recrystallization step, the re-crystallized β-aztreonam typically contains between 1–2% of residual organic solvent and other impurities. A presence of these impurities makes the β-aztreonam less suitable for delivery by inhalation.

A re-crystallization process for preparation of β-aztreonam from α-aztreonam utilizes ethanol as a solvent. Using this process, however, leads to between 5000–10,000 ppm residual ethanol remaining in prepared β-aztreonam. FDA limits a permissible presence of ethanol to less than 5000 ppm. Moreover, over time, the presence of the residual ethanol in β-aztreonam leads to production of ethyl ester, an impurity which is undesirable and not present in the α-aztreonam.

In the process of developing this invention it was unexpectedly found that for preparation of a bulk solution or lyophilized form of aztreonam lysinate for aerosolization or nebulization, α-aztreonam, previously thought to be unstable, was actually a preferred form of a starting material for production of aztreonam lysinate. When compared to the β-aztreonam, the α-aztreonam lysinate was found to contain fewer impurities and the process for its preparation is easier, faster and does not require the use of organic solvents leaving residual impurities.

The α-aztreonam lysinate prepared according to the process of the invention is a substantially pure compound not containing any substantial amount of impurities and contaminants.

3. Solubility of α- and β-Aztreonam

For preparation of pharmaceutical inhalable products, solubility of the active ingredient, in this case aztreonam, in water or acqueous solvents is of importance.

The β-aztreonam is relatively insoluble in water and precipitates into a particular matter and clumps when mixed with water or other acqueous solvent during a dissolution step of the process for preparation of the lysine salt. Such precipitation and clumping leads to increase in impurity at least partially caused by opening of an open-chain nucleophilic ring. In the presence of moisture and under various temperature and humidity conditions, the opening of the open-chain nucleophilic ring increases unpredictably resulting in the compound's higher instability. Testing data shows the initial impurity levels generated by the reaction of the β-aztreonam with lysine salt is in the 1% range and above, close to or above the FDA permissible impurity level.

On the other hand, the impurity levels of α-aztreonam lysinate generated by a direct reaction of α-aztreonam with a lysine salt is less than 0.1%.

α-Aztreonam lysinate prepared according to the process of the invention is a pure compound readily dissolvable in acqueous solvents, saline or water.

4. Comparison of α- and β-Aztreonam Properties

Properties of α- and β-aztreonam and their suitability to be used in a process of manufacturing a bulk solution and lyophilized or dry powder α- and β-aztreonam lysinate for inhalation were studied. During these studies, the following observations were made.

For preparation of aztreonam lysinate suitable fo inhalation, it is important that a starting compound, α- or β-aztreonam, is readily soluble in water and has manageable physiological pH.

a. β-Aztreonam

When studied vis-a-vis the above stated requirements, during manufacturing of bulk solutions for freeze drying and lyophilization, it was found that β-aztreonam cannot be suspended in water at intrinsic pH values because it immediately starts to polymerize and discolor. Independent of temperature, β-aztreonam at concentrations ranging from 50 to 150 mg/ml of water gels within 15 minutes. This eliminates possibility of using reactions whereby a lysine solution would be added to β-aztreonam. The only other possibility for preparation of β-aztreonam lysinate is, therefore, to add β-aztreonam to the lysine solution.

A process of adding β-aztreonam to the lysine solution requires a treatment of β-aztreonam solution with high sheer equipment to achieve rapid dissolution of β-aztreonam before its addition to the lysine solution. In any case, the high pH (around 10) of the lysine solution causes significantly increased formation of certain impurity, herein called impurity B, in the β-aztreonam within short period of time.

Although the above method resulted in manufacturing of β-aztreonam lysinate salt with relatively high but acceptable impurity level, the procedure for its preparation was found not practical for production of β-aztreonam lysinate on a commercial scale, as it involves a rapid addition of β-aztreonam to the lysine solution. Both solutions, that is β-aztreonam and lysine solution, independently, need to be handled with a special equipment and care. β-aztreonam solution requires a high-shear mixer for mixing β-aztreonam and maintaining it in the solution as well as a special dosing equipment for its rapid addition to the lysine solution.

b. α-Aztreonam

On the other hand, α-aztreonam can be easily suspended in water to form a homogeneous slurry, having an acidic pH which enhances its stability. Salt formation can thus be easily performed by adding a lysine solution to the α-aztreonam slurry. This step permits monitoring of the pH during salt formation and the formulation can easily be kept within a pH lower than 6, that is at a pH range offering adequate stability of the formed α-aztreonam lysinate. There is no need for high sheer mixer, dosing or any other equipment.

c. Distinctions Between α- and β-Aztreonam

The important distinction between α- and β-aztreonam is their solubility in water. α-Aztreonam is water soluble at a slightly acidic pH, β-aztreonam is not water soluble and cannot be dissolved at intrinsic pH values.

β-Aztreonam polymerizes, clumps and solidifies when mixed with water without intervention of a high shear mixing equipment. α-aztreonam is readily soluble in water and forms a slurry.

Additionally, β-aztreonam must be added to the lysine solution whereas lysine solution can be added to the α-aztreonam slurry.

Mixing and dosing equipment and a rapid mixing is needed to achieve β-aztreonam dissolution in water and for adding it to the lysine solution. No equipment is needed for dissolution of α-aztreonam in water as the α-aztreonam is readily soluble at the pH lower than 6 and lysine solution can be advantageously added to the α-aztreonam without any substantial pH change.

d. Evaluation of Manufacturing Options

In order to evaluate the manufacturing options for preparation of aztreonam lysinate for inhalation, α-aztreonam and β-aztreonam were used as starting materials to manufacture bulk solutions, dry powder and lyophilizates. The procedures used to manufacture the bulk solutions represent the two obvious possibilities: 1) addition to α- or β-aztreonam to a lysine solution; and 2) addition of the lysine solution to β-aztreonam solution or to α-aztreonam slurry.

The analytical results described below indicate that the addition of a lysine solution to the crystalline form of α-aztreonam offers the most versatile handling options for large scale manufacturing.

C. Development and Optimization of a Manufacturing Process for Preparation of Pure Aztreonam Lysinate for Inhalation In pursuance of the original aim to develop a workable and practical process for large scale manufacturing of aztreonam lysinate for inhalation, both α- and β-aztreonam lysinate were investigated.

1. Materials

All materials used are commercially available. α-aztreonam was obtained from Eutical SpA. β-Aztreonam was obtained from Teva Corp., Israel. Lysine monohydrate was purchased from Merck KGaA. Water was purified by reverse osmosis.

2. Methods

There were two manufacturing processes used for development and optimization of the manufacturing process for preparation of a bulk solution and ultimately for preparation of a lyophilized aztreonam lysinate.

In these studies, two processes are identified as a manufacturing Process I wherein the appropriate amounts of α- or β-aztreonam were added to the lysine solution, and a manufacturing Process II wherein the lysine solution was added to the α- or β-aztreonam.

It was previously determined that for an efficacious inhalable aztreonam product, the bulk solution need to contain about 75 mg/ml of aztreonam lysinate. Consequently, the necessary amounts of aztreonam, lysine and water were calculated such as to reach an optimal aztreonam concentration of 75.0 mg/ml in the bulk solution and an aztreonam to lysine ratio of 1.4:1. The bulk solution need to have pH in around pH 4.8. The batch sizes of the bulk solutions prepared for testing were 200 ml.

Typically, the bulk solution manufacturing and salt formation process were performed within a double jacket glass flask in order to control the temperature throughout the process. The bulk solutions were manufactured according to the following procedures.

3. Manufacturing Processes a) Manufacturing Process I

Manufacturing process I comprises of four steps.

Step 1) A required amount of lysine-monohydrate was weighed and dissolved in an appropriate amount of purified water generated by reverse osmosis using a magnetic stirrer and subsequently filtered through 0.22 μm membrane filter at room temperature (20° C.±2° C.).

Step 2) After complete dissolution of lysine-monohydrate, the lysine solution was brought to 2–8° C. temperature using the refrigerated cooler connected to the double jacket glass flask. The temperature was controlled with a temperature probe in the solution.

Step 3) A necessary amount of α- or β-aztreonam to reach concentration 75 mg/ml was added to the lysine solution under constant stirring and mixing. Mixing was performed by magnetic stirrer in combination with an Ultra Turrax (11,000 rpm, 30 seconds). Preliminary experiments had shown that for β-aztreonam the use of a magnetic stirrer alone leads to unsatisfactory results. This is due to the fact that the low mixing intensity of the magnetic stirrer cannot prevent particles of β-aztreonam to stick to the walls of the flask or to form agglomerates.

Step 4) After addition of the α- or β-aztreonam, mixing was continued until total dissolution occurred (yellowish solution free of particulate matter). During salt conversion, the temperature and pH of the formulation were constantly monitored.

b) Manufacturing Process II

Manufacturing process II comprises of three steps.

Step 1) 50% of the calculated amount of purified water at 2–8° C. was used to form a slurry with α- or β-aztreonam using magnetic stirrer.

Step 2) The necessary amount of lysine-monohydrate was dissolved in the remaining water having the same temperature as the aztreonam slurry and slowly added to the slurry under constant stirring. The addition rate was such that the pH remained lower than pH 6 during the salt conversion.

Step 3) Stirring was continued until a total dissolution of aztreonam occurred. The total dissolution of the aztreonam was identified by a yellow solution free of particulate matter.

c) pH and Temperature Measurements

Since the pH values of dissolved α- and β-aztreonam in water are different, pH and temperature were followed during evaluation of both processes.

Temperature and pH values of test solutions were assessed with an electronic pH-meter equipped with a glass electrode. Before each set of measurements, the pH-meter was calibrated using appropriate standards with pH values of 4.0 and 10.0. Measurements were carried out at the selected temperature for every given experiment. During salt formation, the pH and temperature of the bulk were automatically recorded every 5 seconds.

The bulk solutions of α- or β-aztreonam lysinate were manufactured at different temperatures ranging from 2° C. to 20° C. in order to determine the temperature dependency of the pH of a 75 mg/ml α-aztreonam lysinate solution. Temperature and pH assessment were according to Example 4.

d) Lyophilization

Bulk solutions of α- and β-aztreonam prepared according to manufacturing process I or II were lyophilized and a degree of impurities in each bulk solution and lyophilizate were determined.

To that end, one ml aliquots of the bulk solutions were dispensed into glass lyophilization vials (1.0 mL bulk solution per vial) and lyophilized according to the following conditions.

The shelves of the lyophilizer were prechilled to 0° C. before the start of operations to allow a rapid freezing of the bulk solution in the vials.

Lyophilization vials containing the bulk solution were placed on the prechilled shelves of the lyophilizer. Lyophilizer interior was then chilled to −38° C. at which temperature samples of the bulk solutions in vials were frozen, the temperature of the lyophilizer was maintained at −38° C. and vacuum was adjusted to 0.08 mbar at constant rate within 3 hours. Lyophilizer temperature was then raised to −25° C. within 15 minutes and maintained for 11.75 hours. Vacuum was then adjusted to 0.047 mbar. Temperature was increased to +5° C. within 3 hours and maintained for 12 hours. After 12 hours at +5° C., vacuum was removed, vials were closed and crimped. The process parameters are depicted in FIG. 1.

FIG. 1 illustrates parameters used for lyophilization procedure, specifically it shows time progress, temperature of shelves and the vacuum pressure used for lyophilization.

e. Impurity Analysis

The impurity profiles of the manufactured bulk solutions and lyophilizates were determined by high pressure liquid chromatography (HPLC).

HPLC was carried out using mobile phase A and B. The mobile phase A comprised ammonia formate buffer (pH 3.0) and methanol (94:6). The mobile phase B comprised ammonia formate buffer (pH 3.0) and methanol in ratio 55:45. Reference substances used as standard for detection of impurities were aztreonam; open ring aztreonam; aztreonam E isomer; (Z)-2-(aminothiazole-4-yl)-2-(t-butoxycarbonyl) isopropacyimino acetic acid (ATBA); 2-mercapto-benzothiazole (MBTA) and t-butyl-aztreonam (t-butyl ATR). Standards were prepared as impurity stock solutions and run in parallel with the aztreonam lysinate sample.

HPLC conditions were: 150×3 mm column (4 μm); column temperature 30° C.; sample temperature 10° C.; flow rate 0.6 ml/min; injection volume 40 μl, detection wavelength 270 nm and run time 40 minutes.

Both the aztreonam bulk solutions or lyophilized samples containing different concentrations of aztreonam or aztreonam lysinate were investigated for presence of impurities.

Impurities and degradation products of α- and β-aztreonam were separated by RP-HPLC and detected by UV detection at 270 nm. Quantification was carried out and expressed as area % of all integrated peaks greater than 0.1%.

Impurities profiles for both α- and β-aztreonam lysinates in a graphical form are shown in FIGS. 2-5.

4. Evaluation of the Two Manufacturing Processes

The two aztreonam forms were evaluated by the two manufacturing processes for their conversion to the lysinate salt and the effect of the selected process on purity levels and stability.

a. Salt Conversion

Conversion of α- or β-aztreonam into its lysine salt, as described above, depends on the starting form of aztreonam as well as on the manufacturing process used.

α-aztreonam was found to be compatible with both manufacturing processes. This was due to the fact that α-aztreonam can be suspended in water without solidifying, a problem observed with β-aztreonam. Because β-aztreonam solidifies nearly immediately when added to water, the salt conversion upon addition of lysine solution took longer and relatively high degree of degradation of β-aztreonam was observed.

Table 1 summarizes the findings regarding the salt conversion step.

TABLE 1

Salt Conversion

| | Manufacturing Process I | Manufacturing Process II |
|---|---|---|
| α-Aztreonam lysinate | No unusual occurrence during salt conversion Yellowish, slightly opalescent solution | No unusual occurrence during salt conversion Yellowish, slightly opalescent solution |
| β-Aztreonam lysinate | No unusual occurrence during salt conversion Clear, yellowish solution | ATR-slurry partly solidified (within 30 secs) before lysine addition. Therefore slow salt conversion upon addition of lysine solution Clear, pinkish solution |

ATR is used as an abbreviation for aztreonam.

Results show that when using α-aztreonam, the more simple manufacturing process II can be used for the lysine salt production without any consequences. When the starting aztreonam is β-aztreonam, the manufacturing process I needs to be used for the salt conversion. When used for preparation of β-aztreonam lysinate, the process II results in impure and unstable aztreonam lysinate. On the other hand, the process I requires more complicated and expensive equipment and because of the presence of impurities, it requires also more extensive validation work, especially when aztreonam lysinate is prepared on a large production scale.

b. Aztreonam Content in Bulk Solutions

The aztreonam contents found in the bulk solutions manufactured by the processes I and II with starting concentration of aztreonam of 75.0 mg/ml, immediately after manufacturing are summarized in Table 2.

TABLE 2

Aztreonam Content of Bulk Solutions

| | Aztreonam Content (mg/mL) | |
|---|---|---|
| | Bulk Manufacturing Process I | Bulk Manufacturing Process II |
| α-Aztreonam lysinate | 74.7 | 74.7 |
| β-Aztreonam lysinate | 74.0 | 62.9 |

Aztreonam content is mean of 2 injections per solution.

As seen in Table 2, there is only small loss observed in both aztreonam forms when the process I is used. When the process II is used, the same amount of α-aztreonam is present in the bulk solution as in the bulk solution prepared by the process I. However, the results seen in Table 2 indicate that there is a significant degradation of β-aztreonam when following the manufacturing process II. This is at least partly due to the solidifying of β-aztreonam observed during manufacturing process II where upon the dissolution in water the total surface area of β-aztreonam is reduced and the salt conversion and dissolution is slower compared to α-aztreonam under the same conditions. Degradation reactions of β-aztreonam which are pH dependent occur. This phenomenon is not observed with α-aztreonam that, as pointed out above, is easily dissolved in water at pH under pH 6.0. As described above, α-aztreonam dissolved in water forms a homogeneous slurry having a large surface area.

c. Lyophilization

Lyophilization conditions used for preparation of lyophilized α-aztreonam and β-aztreonam were suitable for both forms of aztreonam.

No significant differences between the two aztreonam forms were observed during freeze drying operations. All freeze-dried residues looked homogeneous without any wet, shrinked or sintered areas observed at the bottom of the lyophilization vials. Furthermore, no aztreonam particles were found on the vial walls, indicating that adequate temperature, pressure and ramping rates were used during freeze drying. The dissolution rate for both lyophilized aztreonams was very good with a reconstitution of both freeze-dried residues occurring in less than 1 sec after addition of solvent (0.17% saline/1.0 ml).

The selected freeze drying cycle lead to lyophilizates with generally low water contents of between 0.3–0.5%. As the water content in the final freeze-dried aztreonam lysinate could be raised to around 2.0% without stability problems, the cycle duration could be further shortened to approximately 30 hours.

Table 3 summarizes the water contents of the two lyophilizates.

TABLE 3

Water Content in the Lyophilizates

| | Water Content in the Lyophilizates (%) | |
|---|---|---|
| | Bulk Manufacturing Process I | Bulk Manufacturing Process II |
| α-Aztreonam lysinate lyophilizates | 0.5% | 0.4% |
| β-Aztreonam lysinate lyophilizates | 0.3% | 0.3% |

Water content in the lyophilizates is mean of 3 vials per batch.

Water content in both aztreonam lysinate lyophilizates is well under the acceptable level of water (2.0%) which could affect the aztreonam lysinate stability.

The aztreonam content in the lyophilization vials after lyophilization of both forms of aztreonam lysinates prepared by the processes I and II is summarized in Table 4.

TABLE 4

Aztreonam Content per Vial After Lyophilization

| | Aztreonam Content/Vial (mg) | |
|---|---|---|
| | Bulk Manufacturing Process I | Bulk Manufacturing Process II |
| α-Aztreonam lysinate lyophilizates | 73.8 | 74.0 |
| β-Aztreonam lysinate lyophilizates | 73.1 | 60.9 |

Aztreonam content is mean of 3 vials.

As expected from the bulk solution results seen in Table 2, lyophilizates made of β-aztreonam following the manufacturing process II contain much less than 75.0 mg aztreonam. There is a significant loss of approximately 12% of β-aztreonam during manufacturing process II. The results obtained from the lyophilization process indicate, that no significant loss of either of the aztreonams occurs during the freeze drying operation. The small decrease in amount of aztreonams observed in Table 4 compared to amounts seen in Table 2 is attributed to dispensing operations and to the reconstitution of the cakes prior to analysis. Therefore, the lyophilization cycle and its ramping rates can be regarded as valid for the bulk solution/vial combination.

d. Analysis of Total Impurities of α- and β-Aztreonam

Analysis of total impurities in the two aztreonam forms is shown in FIGS. 2–5 and Table 5.

Figure 2:
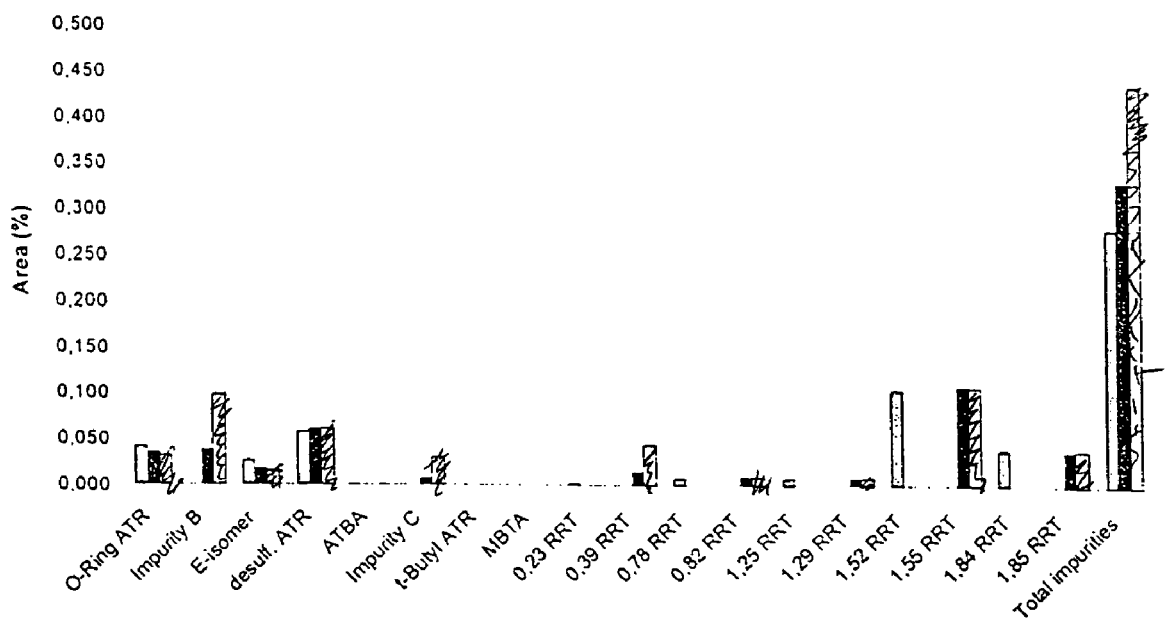
FIG. 2 is a graph showing impurity analysis of bulk solutions and lyophilizates of α-aztreonam prepared according to manufacturing procedure I compared to aztreonam free acid expressed as an active pharmaceutical ingredient (API).

FIG. 2 shows impurity analysis of bulk solutions and lyophilizates of α-aztreonam lysinate manufactured by manufacturing process I compared to the aztreonam active pharmaceutical ingredient (API). As seen in the last column of FIG. 2, the total impurities observed in α-aztreonam lysinate in the API were 0.280%, in the bulk solution were 0.332% and total impurities in lyophilizates reaching 0.436% of the area.

Figure 3:
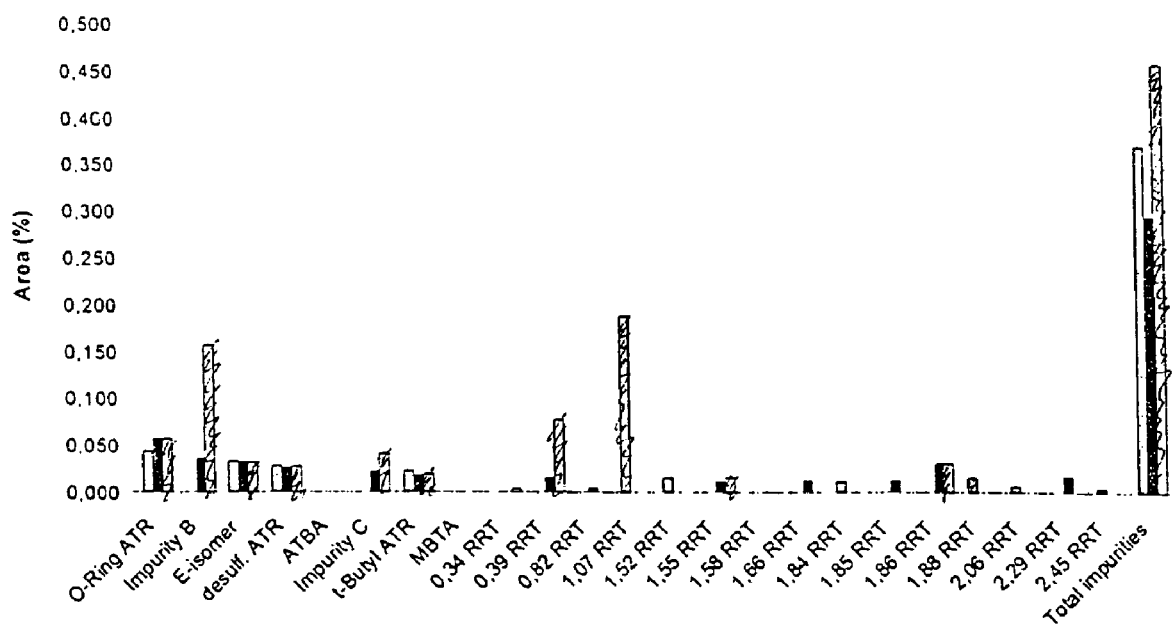
FIG. 3 is a graph showing impurity analysis of bulk solutions and lyophilizates of β-aztreonam prepared according to manufacturing procedure I compared to aztreonam free acid expressed as an active pharmaceutical ingredient (API).

FIG. 3 shows impurity analysis of bulk solution and lyophilizates of β-aztreonam lysinate manufactured by manufacturing process I compared to API. As seen in the last column of FIG. 3, total impurities in the API were 0.370%, in the β-aztreonam bulk solution were 0.295% of area and the impurities found in lyophilizates were 0.457% of the area.

Observed levels of impurities in the α- and β-aztreonam were approximately the same for both aztreonam forms.

Figure 4:
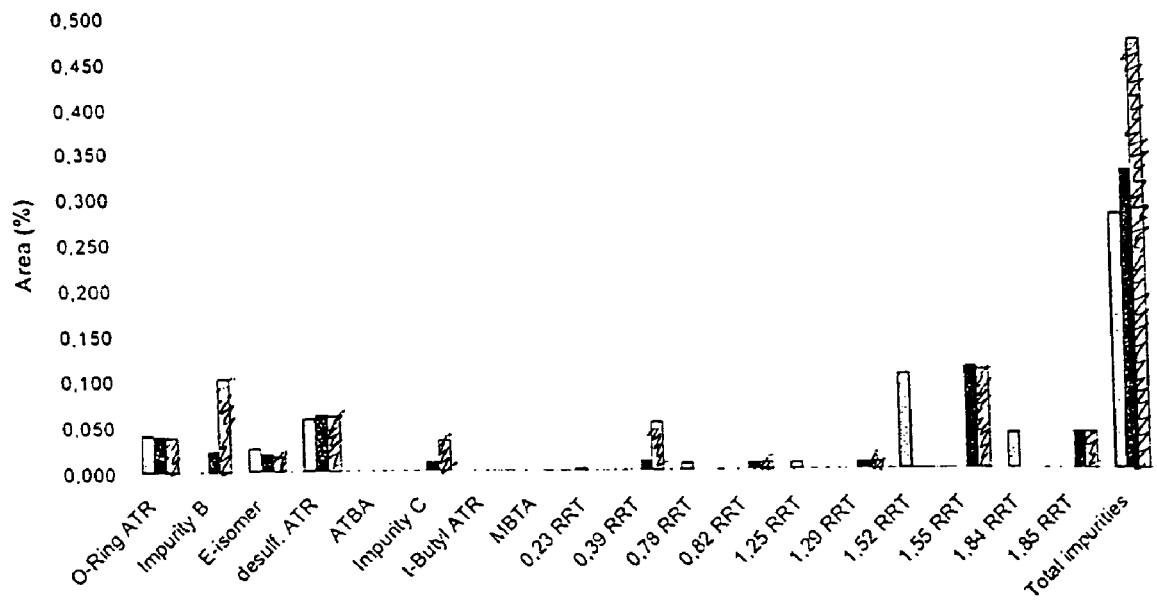
FIG. 4 is a graph showing impurity analysis of bulk solutions and lyophilizates of α-aztreonam prepared according to manufacturing procedure II compared to aztreonam free acid expressed as an active pharmaceutical ingredient (API).

FIG. 4 shows impurity analysis of the bulk solutions and lyophilizates of α-aztreonam prepared by manufacturing process II. As seen in FIG. 4, the total impurities present in the API were 0.280%, in the bulk solution were 0.328% of the area and total impurities in lyophilizates were 0.471% of the area.

Figure 5:
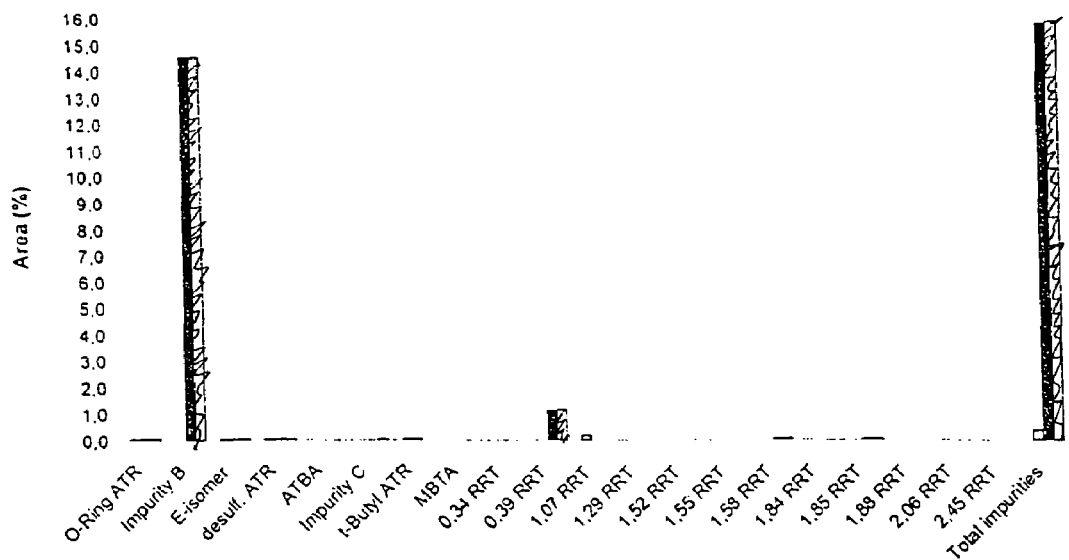
FIG. 5 is a graph showing impurity analysis of bulk solutions and lyophilizates of β-aztreonam prepared according to manufacturing procedure II compared to aztreonam free acid expressed as an active pharmaceutical ingredient (API).

FIG. 5 shows analysis of the bulk solution and lyophilizates of β-aztreonam compared to API prepared by the manufacturing process II. As seen in FIG. 5, the impurities detected in API were 0.370%, which roughly corresponds to levels detected in FIGS. 2, 3, and 4. Levels of impurities detected in the β-aztreonam bulk solutions and lyophilizates were extremely high. Both the bulk solution and the lyophilizate of β-aztreonam produced by manufacturing process II contained 15,812% of the area in the bulk solution and 15,867% of the area in the lyophilizates.

Compared to the total impurities observed in the α-aztreonam bulk solution and lyophilizate, the levels of impurities in the β-aztreonam were almost 34 times higher in lyophilizates and 48 times higher in the bulk solutions.

Table 5 summarizes the obtained data for levels of impurities present in the bulk solutions and lyophilizates for α- and β-aztreonam lysinates.

TABLE 5

| | Total Impurities | | | |
|---|---|---|---|---|
| | Bulk Solutions | | Lyophilizates | |
| | α-aztreonam lysinate | β-aztreonam lysinate | α-aztreonam lysinate | β-aztreonam lysinate |
| Manufacturing Procedure I | 0.332% | 0.295% | 0.436% | 0.457% |
| Manufacturing Procedure II | 0.328% | 15.912% | 0.471% | 15.867% |

Impurities are expressed as a percentage of the area.

When using α-aztreonam as active pharmaceutical ingredient (API), no significant differences can be found between manufacturing processes I and II. The bulk solutions have an impurity level of around 0.33 area %, which represents an increase of around 0.04–0.05% versus the API. The lyophilizates have total impurities of around 0.45 area %, which represents an increase of around 0.08–0.12% versus API. It is important to emphasize that most single impurities found after manufacturing α-aztreonam lysinate using the described manufacturing processes I and II are below the level of 0.1%. And consequently, both processes may be conveniently used for manufacturing α-aztreonam lysinate. When using the 0.1% FDA reporting limit, the α-aztreonam bulk solutions and lyophilizates would have impurity levels of 0.1% only. This is significantly less than the impurity levels found in AZACTAM® (commercially available aztreonam arginine), which contains 1.6% total impurities.

β-Aztreonam lysinate can be successfully manufactured form β-aztreonam according to the manufacturing process I, where the total impurities in the bulk solution are around 0.3% and around 0.45% in the lyophilizates. This represents an increase of around 0.1% versus API. However, when the manufacturing process II is used for preparation of β-aztreonam, the impurity level in the bulk solution is around 15.8%. After lyophilization, the impurity level remains unchanged. The analysis of the impurities profile show that the high impurity level in the β-aztreonam is mainly due to generation of the impurity B and a second unknown impurity, both generated during β-aztreonam lysinate salt conversion process. All other impurities typically found in the β-aztreonam bulk solutions and lyophilizates also remain lower than 0.1%.

These results indicate that the manufacturing process II is not a most suitable process for preparation of β-aztreonam lysinate. Not only it leads to the high increase in impurities but it also requires a dedicated manufacturing procedure and the costly equipment for production of the bulk solution. However, when the β-aztreonam lysinate is desired as a final product, the manufacturing process I is suitable to produce the product with the acceptable degree of impurities.

As is seen from these results, α-aztreonam offers a major advantage for manufacturing α-aztreonam lysinate over β-aztreonam lysinate. α-Aztreonam can easily be suspended in water, forming a homogeneous suspension without need for any special equipment allowing a lysine solution to be added to the α-aztreonam.

Therefore, the bulk solutions and lyophilizates for α-aztreonam lysinate containing about 75 mg/mL can be manufactured in a straightforward, practical, fast, easy and inexpensive way.

D. Advantages of α-Aztreonam Lysinate

Since the aztreonam containing arginine is not suitable for inhalation, other acid addition salts were prepared and tested. Aztreonam lysinate, particularly aztreonam lysinate derived from α-aztreonam form, was found to be pharmacologically most safe, acceptable and efficacious for inhalation purposes when administered by nebulization as a dry powder or aerosolized lyophilizates in amounts of about 75 mg/ml.

The prior art process dealing with α- and β-aztreonams involved conversion of α-aztreonam to β-aztreonam. In order to yield the aztreonam lysinate as a final product, such conversion step, if used for production of bulk or lyophilized aztreonam lysinate, necessarily involves reacting the β-aztreonam being relatively insoluble in water and having a pH of approximately pH 2.3, with the lysine salt having a pH of approximately pH 10. The addition of the lysine salt component to β-aztreonam creates excessive ion exchange during the titration of the aztreonam acid to a physiologically acceptable pH. Additionally, this reaction results in an undesirable side reaction with open chain formation of the β-lactam ring in the aztreonam, further leading to β-aztreonam lysinate having a higher degree of impurity, instability and an undesirably high osmolality.

High osmolality is not desirable for the inhalable aztreonam. The inhalable aztreonam formulation requires very specific degree and range of osmolality because the high osmolality of the inhalable formulation may cause a patient to react to the inhalation with bronchospasm or cough.

In the current invention, the preferred pharmaceutically acceptable aztreonam lysinate salt is derived from a direct reaction of α-aztreonam with lysine without need of conversion of α-aztreonam to β-aztreonam first.

The production of α-aztreonam lysinate derived from α-aztreonam form without converting α-aztreonam into β-aztreonam is a novel process not disclosed or suggested by any prior art.

The currently disclosed process for manufacturing a bulk solution or lyophilized α-aztreonam lysinate for inhalation is based on the finding that α-aztreonam, when solubilized in water and stirred, immediately forms an emulsion or smooth slurry. When a lysine salt solution is titrated to the slurry, a rapid formation of an amorphous α-aztreonam lysine salt results. This salt has similar stability characteristics to the lyophilized β-aztreonam lysinate without, however, a detrimental increase in the impurities observed during a β-aztreonam lysinate production. The reaction with lysine, lyophilization and drying of the α-aztreonam lysinate does not cause the opening of the nucleophilic ring and thus the initial impurity levels generated from the alpha form is less than 0.1%, substantially less than the FDA limit for the permitted level of impurities.

Therefore, by using the α-aztreonam directly for formation of α-aztreonam lysinate, the obtained product contains much lower initial impurity levels, has a higher stability and over time shows lesser degradation thereby leading to the product with a longer shelf life.

In the current process for preparation of α-aztreonam lysinate from α-aztreonam, the basic salt conversion volumes, ratio of individual components and pH of the reaction mixture are titrated to a fixed level. The titration process confirms that less than 100 ppm of residual ethanol in the α-aztreonam lysinate remains using the manufacturing process II compared to the manufacturing of β-aztreonam lysinate where in the same reaction volume the residual ethanol levels up to 10,000 ppm were detected. These levels are approximately 100 times higher than those observed during preparation of α-aztreonam lysinate. Moreover, by using the α-aztreonam, the formation of ethyl ester, another impurity detected in the β-aztreonam forms is eliminated.

Concerning the stability of the two formulations, the accelerated stability conditions shows that the β-aztreonam degrades from the initial 0.9% open chain to over 2% at 30 days whereas α-aztreonam degrades from an initial 0.06% to only 1.2% in 90 days under the same testing conditions.

Consequently, the use of the α-aztreonam and preparation of the α-aztreonam lysinate using the manufacturing process II produces a more stable product with a better pH profile, lower impurity content, longer stability and a desirably reduced osmolality.

E. Process for Manufacturing of α-Aztreonam Lysinate

Three potential techniques were developed to yield the α-aztreonam lysinate derived from the α-aztreonam. The first technique involves titration of lysine salt into the α-aztreonam. The second techniques involves vacuum-drying of the raw α-aztreonam at the end point of the synthesis when the aztreonam is combined with lysine in a lyophilizer. In the third technique, α-aztreonam lysinate is produced directly. The third technique involves spray-drying of the α-aztreonam and lysine into a bulk solid producing the aztreonam lysinate as the final product. All these techniques avoid conversion of the α-aztreonam to the β-aztreonam.

The current preferred process for preparation of the aztreonam lysinate derived from α-aztreonam comprises solubilization of α-aztreonam in water and subsequent titration of an aqueous solution of lysine into the α-aztreonam to form the lysine salt. The mixture is then lyophilized or spray dried.

The current process avoids cleavage of the β-lactam ring by advantageously employing a titration to achieve a desirable pH profile of the α-aztreonam lysinate which is contrary to the techniques used for β-aztreonam lysine salt preparation.

In either of the techniques disclosed herein for preparation of the α-aztreonam lysinate derived from the α-aztreonam, a conversion to the β-aztreonam as well as all problems connected with production of the β-aztreonam lysinate derived from the β-aztreonam are avoided.

a. α-Aztreonam Lysinate Manufacturing Process

Manufacturing process for preparation of a bulk solutions of α-aztreonam lysinate comprising about 75 mg of α-aztreonam per one ml of water or another aqueous solvent is essentially based on the previously described manufacturing process II. The process involves reaction of components listed below in Table 6.

TABLE 6

| Components | mg per 1 ml Unit |
| --- | --- |
| α-Aztreonam | 75 mg |
| Lysine monohydrate | 52.5 mg |
| Water for injection | up to 1 mL |
| Nitrogen | qs |

For preparation of one liter of α-aztreonam lysinate, 75 grams of α-aztreonam and 52.5 grams of lysine monohydrate are dissolved in one liter of water for injection. For a large scale preparations of α-aztreonam lysinate, these amounts are appropriately multiplied.

Specifically, the process steps for preparation of the bulk solution are as follows. Approximately 400 ml of water for injection (WFI) is added to a mixing vessel, the mixing vessel is cooled to a temperature between 2 and 8° C. and 52.5 grams of lysine monohydrate is added to the water. The temperature is maintained between 2 and 8° C. The mixture is then stirred until clear. The solution is brought to 500 ml volume with water for injection.

Separately, 400 ml of water for injection is added to the second mixing vessel and cooled to between to 2 to 8° C. and 75 grams of anhydrous α-aztreonam is suspended in the cooled water under rapid stirring and cooling to keep the temperature under 10° C. The actual amount of α-aztreonam, which typically may contains up to 15% of moisture, is adjusted such as to correspond to 75 grams of anhydrous α-aztreonam. Then the calculated amount of the lysine solution is titrated over relatively short period of time between about 1 and 15 minutes, preferably in about 6 minutes, into the aztreonam suspension while maintaining the temperature constantly below 10° C. and the pH equal to or less than 6.0. The pH of the solution is measured and adjusted, if needed, with lysine monohydrate solution to a final pH of 4.8+/−0.5. The solution is brought to volume with water for injection and mixed until clear. The final volume of both the lysine solution and α-aztreonam solution, combined, should be one liter.

After verifying that the pH and assay results are within specification, the solution is filtered by means of peristaltic pump through a prefilter, preferably 0.45 μm prefilter, and through two additional filters, preferably of size of about 0.1 to about 0.3 μm, preferably a 0.22 μm hydrophilic Millidisk 40 cartridge filter, into the receiving vessel that is maintained under filtered (0.22 μm) nitrogen flow. The integrity of the final (0.22 μm) filter is tested after filtration. The receiving vessel is maintained at a temperature lower than 10° C. Post-filtration samples are tested for the amount of α-aztreonam lysinate, contamination, density and appearance.

The visual appearance of the α-aztreonam lysinate bulk solution was as a yellowish solution free of particulate matter. The pH of the bulk solution was 4.82. Viscosity, surface tension and osmolality were 1.55 mPas, 67.11 mN/m and 410 mOsmol/kg, respectively. Total impurities were 0.328%.

The filtered solution is filled into amber glass vials with a 1 mL±10% fill volume. Fill volume are checked every 15 minutes. Vials are equipped with stoppers left in the open position and placed in the lyophilizer.

Lyophilization is performed according to three step exemplary lyophilization conditions summarized in Table 7.

TABLE 7

Lyophilization Conditions

| Step | Procedure | Lyophilization Process |
|---|---|---|
| 1 | Product freezing | Freezing conditions:<br>Shelves chilled: <−46° C.<br>The product frozen at −10° C. ± 3° C.<br>with no vacuum and held for two hours |
| 2 | Primary drying | Drying conditions:<br>1 hour: −40° C. ± 3° C. and at ≦80 microbar<br>At least 15 hours: −25° C. ± 3° C. and ≦80 microbar<br>Temperature ramped to 25° C. ± 3° C. with a gradient of 10° C./hour |
| 3 | Secondary drying | Drying conditions:<br>At least 10 hours: 25° C. ± 3° C. and ≦80 microbar and until product reaches 25° C. ± 3° C.<br>The vacuum broken with sterile nitrogen |

Alternatively, the lyophilization cycle can be performed under different conditions, such as for example, conditions listed in Table 8.

TABLE 8

Lyophilization Conditions

| Step | Procedure | Lyophilization Process |
|---|---|---|
| 1 | Product freezing | Freezing conditions:<br>Shelves chilled: −38° C.<br>The product frozen at −35° C. ± 3° C. with no vacuum and held for four hours |
| 2 | Primary drying | Drying conditions:<br>Vacuum started at ≦80 microbar<br>Temperature decreased to −25° C. ± 3° C. and held for 8 hours at ≦80 microbar |
| 3 | Secondary drying | Drying conditions:<br>Vacuum adjusted to ≦47 microbar<br>Temperature ramped to +25° C. ± 3° C. and held for 16 hours Cycle ended, vials closed, vacuum broken |

In the second cycle for lyophilization, the vials are closed within the lyophilizer under vacuum, at the end of the secondary drying.

It is to be understood that any variation in the lyophilization process is intended to be within the scope of this invention.

Throughout the whole manufacturing process, water content and visual inspection tests are performed. Following the lyophilization, the vials are completely closed with stoppers and fitted with aluminum crimp caps. Vials are visually checked for effective capping every 15 minutes during the capping and sealing process.

The lyophilized vials are kept and stored at the temperature between about −20° C. and 8° C. which was found to be the optimal temperature for lyophilized product stability. Additionally, this temperature was found to be the most optimal temperature for maintaining the stability of the product during manufacturing.

Manufacturing process II used for manufacturing of α-aztreonam lysinate has been described above and the impurities profile is illustrated in FIG. 4. The total impurities observed during a large scale manufacturing of α-aztreonam lysinate according to the process II are only slightly higher than impurities seen in API. Specifically, only traces (0.014%) of impurity B can be detected in α-aztreonam lysinate product and represent a 5 fold reduction in that particular impurity compared to the β-aztreonam bulk solutions and lyophilizates.

The visual appearance of the α-aztreonam lyophilizates was as a yellowish solution free of particulate matter. The pH of the lyophilizate was 4.78. Viscosity, surface tension and osmolality were 1.5 mPas, 70.34 mN/m and 430 mOsmol/kg, respectively. Total impurities were 0.471%. These results were reproducible in three independent runs of α-aztreonam lysinate manufacturing batches.

To confirm that the manufacturing process II represent the optimal conditions for manufacturing of α-aztreonam lysinate for inhalable purposes, investigations of the effect of the pH, temperature and bulk solution concentrations were performed. Further, the stability of the lyophilized product as well as the diluted product was also evaluated.

b. Evaluation of Effect of pH and Temperature

Since the pH values played such an important role in distinction between α and β-aztreonam, pH and temperature effect was evaluated for optimization of the manufacturing process for manufacturing of α-aztreonam lysinate.

Briefly, α-aztreonam lysinate (75 mg/ml) at pH 4.8 at 20° C. was cooled to 10° C. and 2° C. and the pH was measured every 5 seconds. There was no significant impact of the cooling to a temperature of 10 or 2° C. on the pH of the α-aztreonam lysinate bulk solution. Consequently, the manufacturing process can conveniently be performed at temperatures between 2 and 20° C., however, as stated above, the process is optimally performed at 2–8° C.

Additionally, as already described above, α-aztreonam is readily dissolvable in water without polymerization, discoloration, solidifying and gelling, permitting a lysine solution to be added to the α-aztreonam solution without encountering high pH values during the process.

Aztreonam stability is pH dependent. Maximum stability of aztreonam is in a pH range between pH 4.2 and 7, with the optimal pH range being between 4.6 and 4.8. As described above, the pH of the α-aztreonam falls within the optimal pH range.

c. Influence of Bulk Solutions on the Impurity Profile

Optimal concentration for amount of aztreonam in the aerosol is 75 about mg/ml, although the concentration of the aztreonam may differ, that is to be smaller or larger, depending on the therapeutic requirement for treatment of different conditions. To optimize the manufacturing process changes in concentration of aztreonam in the bulk solutions were investigated vis-a-vis limitations set by the freeze-drying process, the amount of water to be removed during the freeze drying and by the shape and size of the lyophilization vial where the product is stored.

Typically, low concentration lead to physically unstable product and high concentrations of the active ingredient compound in the bulk solution can be detrimental to the overall drying process. The shape and size of vials have an impact on the volume of the bulk solution and the concentration of the active ingredient therein.

When the bulk solutions of 25, 37.5 and 75 mg/ml of α-aztreonam lysinate were investigated for a level of impurities, the purest bulk solution was obtained at 37.5 mg/ml concentration. However, α-aztreonam at the 75 mg/ml concentration was found to have only slightly higher level of impurities and this level of impurities was at acceptable levels below or around 0.1% of impurities and, most importantly, the drug concentration met the required amount of the active compound needed for inhalation product.

d. α-Aztreonam Stability

Alpha aztreonam, compared to β-aztreonam, permits production of aztreonam lysinate with a higher purity, better stability and longer shelf-life.

The α-aztreonam has advantages of better dispersion in water and lower residual ethanol (100 ppm) content than the β-aztreonam (10,000 ppm). This property results in lower total impurities during the salt conversion. Using the α- or β-aztreonam at the beginning of the manufacturing process results in the same comparable final drug product, an amorphous aztreonam salt, each however, having a different level of impurities and stability.

Two lots of drug product were produced using the β-aztreonam and one lot of drug product was produced using the α-aztreonam. The three lots of drug product were evaluated for stability at the time of the product manufacture (total initial impurities) and at 6 months after the manufacture (total impurities at 6 months) in the product stored under refrigeration at 5° C. The total impurity results for the lots are listed in the Table 8.

TABLE 8

Total Impurities

| Aztreonam form | Total initial impurities | Total impurities at 6 months |
|---|---|---|
| Drug product 1 | β-aztreonam lysinate | 1.23% | 1.47% |
| Drug product 2 | β-aztreonam lysinate | 1.27% | 1.35% |
| Drug product 3 | α-aztreonam lysinate | 0.65% | 0.84% |

The initial total impurities for the drug product (aztreonam lysinate) produced from β-aztreonam were 1.23% and 1.27%, respectively, as measured by HPLC, whereas the initial total impurities for the drug product produced from α-aztreonam were 0.65%. After 6 months of storage at 5° C., total impurities for β-aztreonam lysinate were 1.47% and 1.35%, respectively, whereas the total impurities for α-aztreonam lysinate were 0.84%.

Since the likely limit of impurities for the final product at a time of administration is 2%, the α-aztreonam lysinate is a better candidate for a stable product and thus a preferred aztreonam form leading to a product with a longer shelf life than the β-aztreonam lysinate, although β-aztreonam has also acceptable level of impurities.

e. Stability of the Diluted α-Aztreonam

Since the inhalable α-aztreonam lysinate is, in one mode, delivered as an aerosolable solution, its stability in the solution was determined.

To that effect, α-aztreonam lysinate samples taken from the bulk solutions were diluted with a buffer at a ratio of 1:250. Samples were then investigated at a time zero (freshly prepared), after 1, 3, 6 and 12 hours and impurity profiles were determined.

The diluted samples of α-aztreonam lysinate were found to be stable for the entire 12 hours, with only negligible increases in impurities toward the 12 hour limit.

These finding show that there is a good stability of the α-aztreonam lysinate in a diluted state and that there is no rapid degradation of the α-aztreonam lysinate when the lyophilized product is diluted before its use as an inhalation product.

f. Reconstitution of Lyophilized α-Aztreonam Lysinate

The impurity profile for reconstituted samples of lyophilized α-aztreonam lysinate was determined.

For this purpose, the lyophilizates were reconstituted with 1 ml of the 0.17% saline and visual appearance, pH, viscosity, surface tension, osmolality and total impurities were determined.

The visual appearance of the α-aztreonam lysinate lyophilizate was as a yellowish solution free of particulate matter. The lyophilizate's pH was 4.78. Viscosity, surface tension and osmolality were 1.5±0.16 mPas, 70.34±0.2 mN/m and 430 mOsmol/kg, respectively. Total impurities were 0.601%.

Osmolality of the inhalable product is extremely important. High osmolality is not desirable for the inhalable aztreonam as it is not tolerated by patients with respiratory infections. The inhalable aztreonam formulation requires very specific degree and range of osmolality because the high osmolality of the inhalable formulation may cause a patient to react to the inhalation with bronchospasm or cough.

It is therefore of great importance that both the lyophilized and reconstituted lyophilized α-aztreonam lysinate have acceptable osmolality in the range of around 400–550 mOsml/kg.

Figure 6:
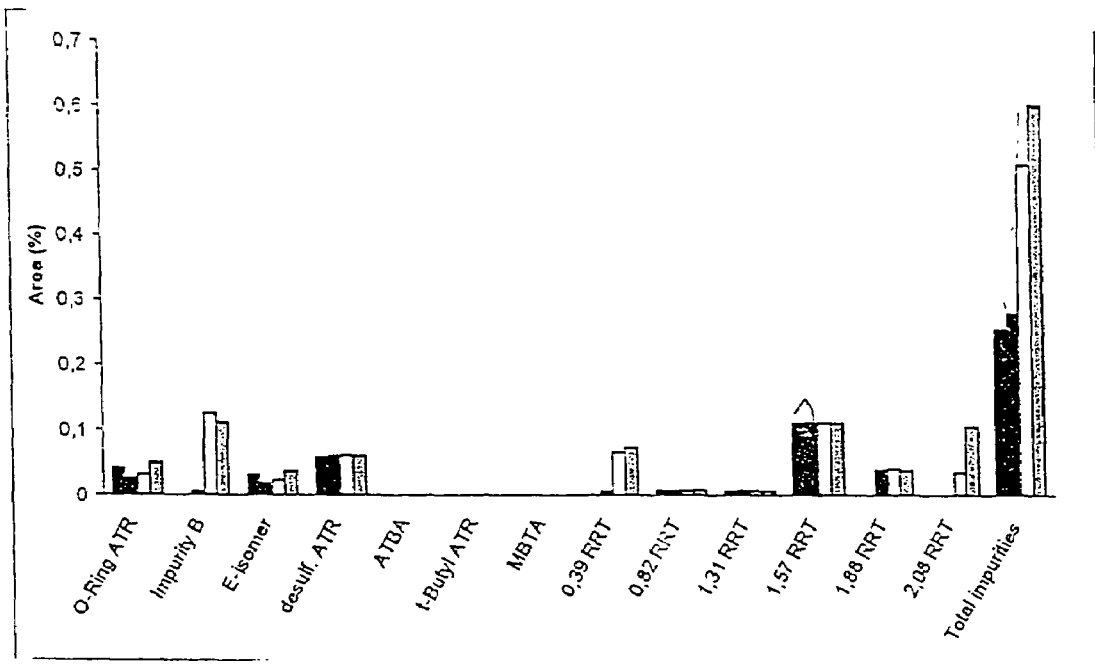
FIG. 6 is a graph showing impurity analysis of bulk solutions, lyophilizates and reconstituted lyophilizates of α-aztreonam prepared according to the manufacturing procedure II compared to aztreonam free acid expressed as an active pharmaceutical ingredient (API).
Figure 1:
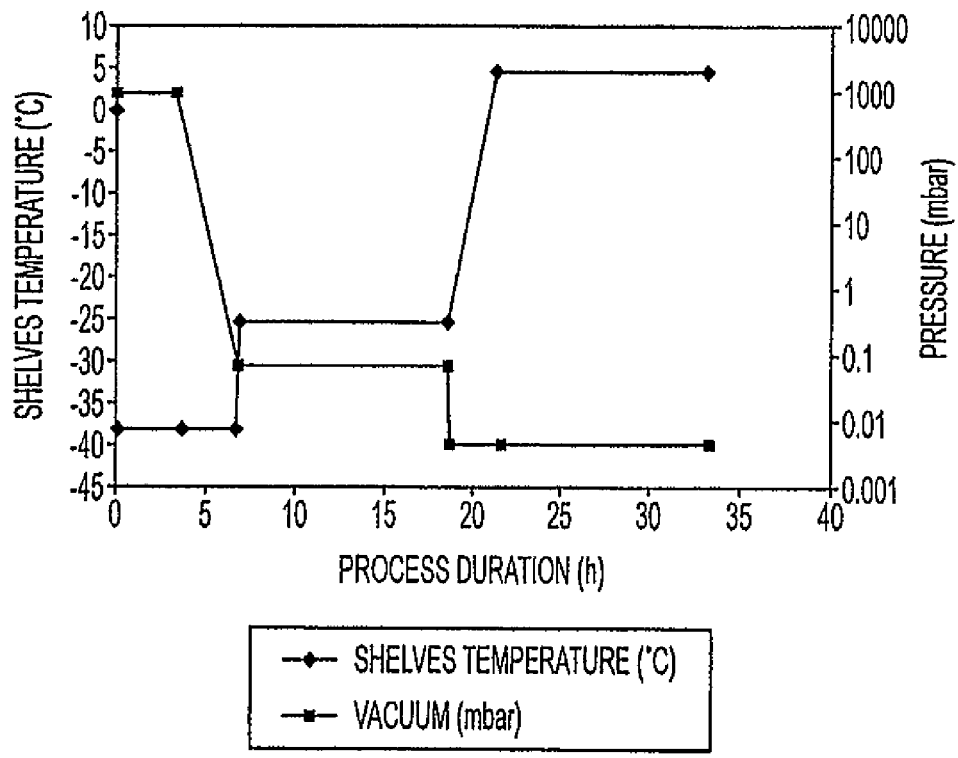
Figure 2:
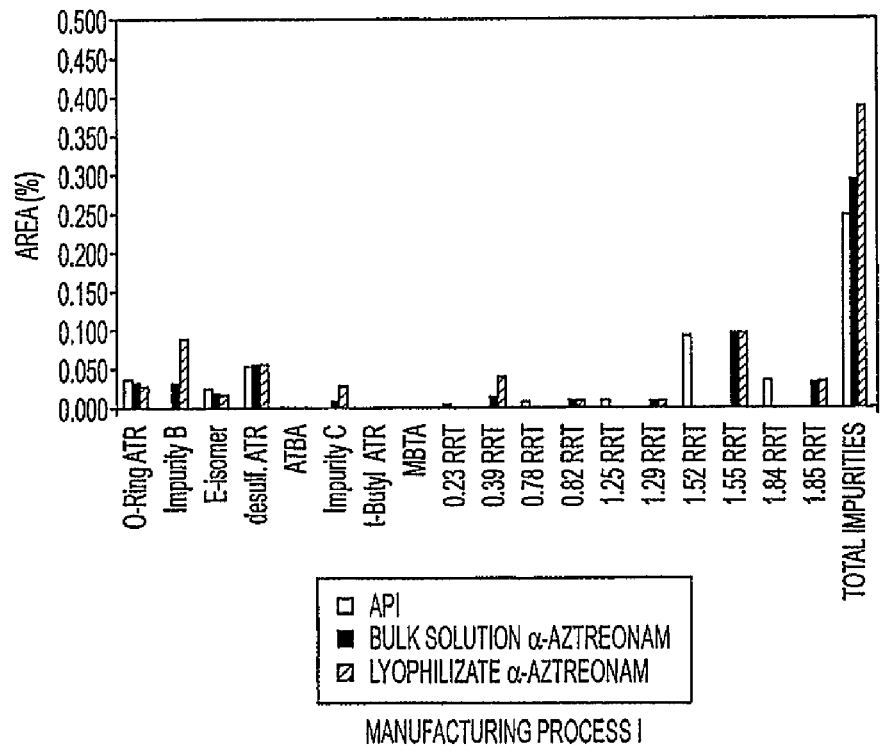
Figure 3:
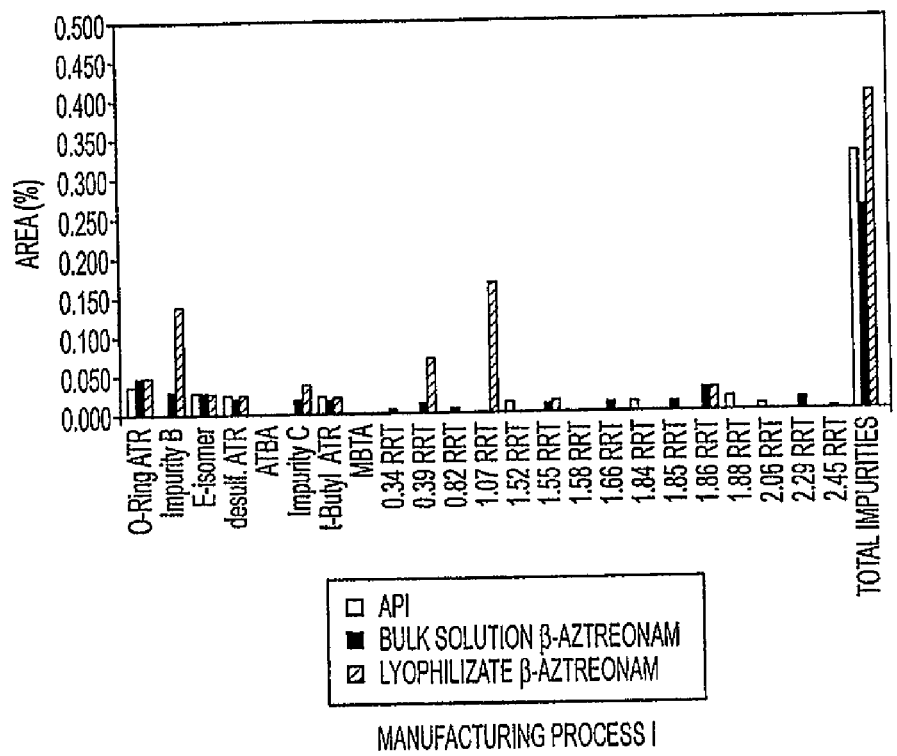
Figure 4:
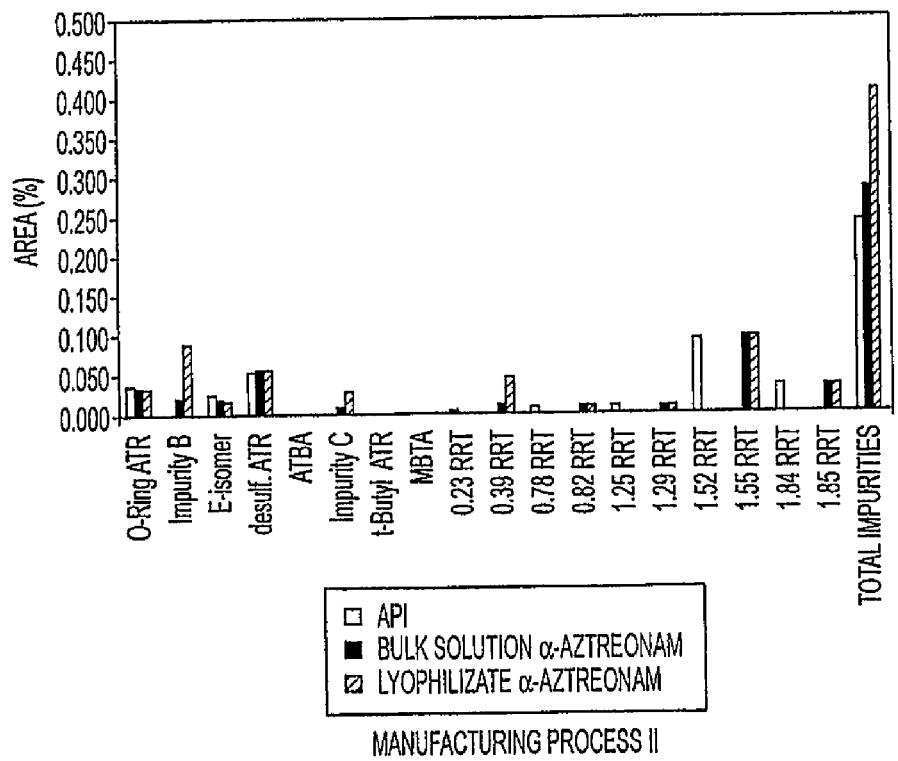
Figure 5:
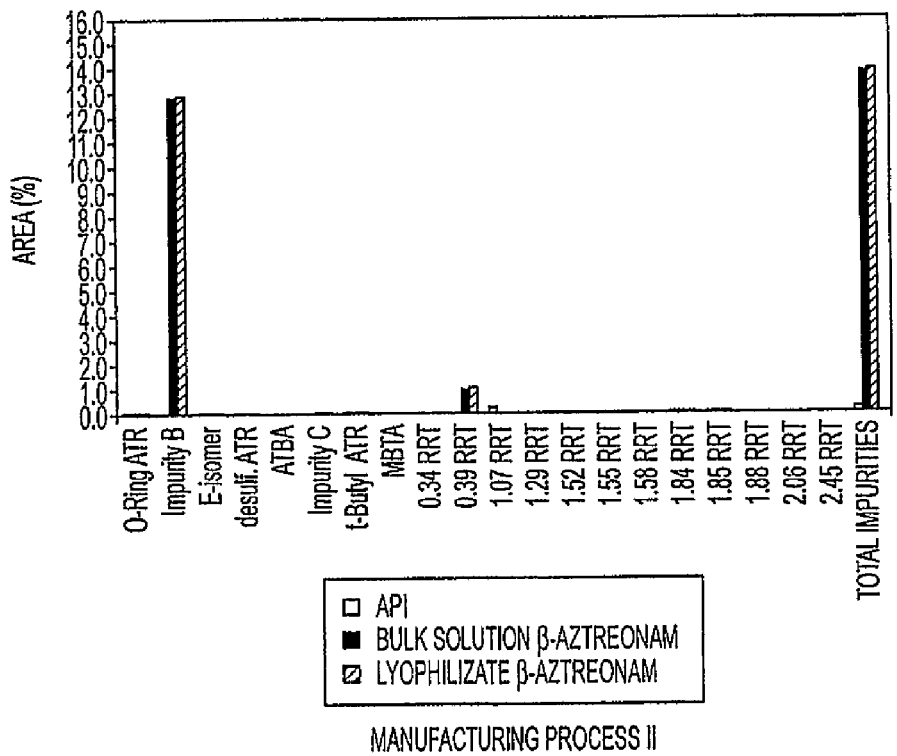
Figure 6:
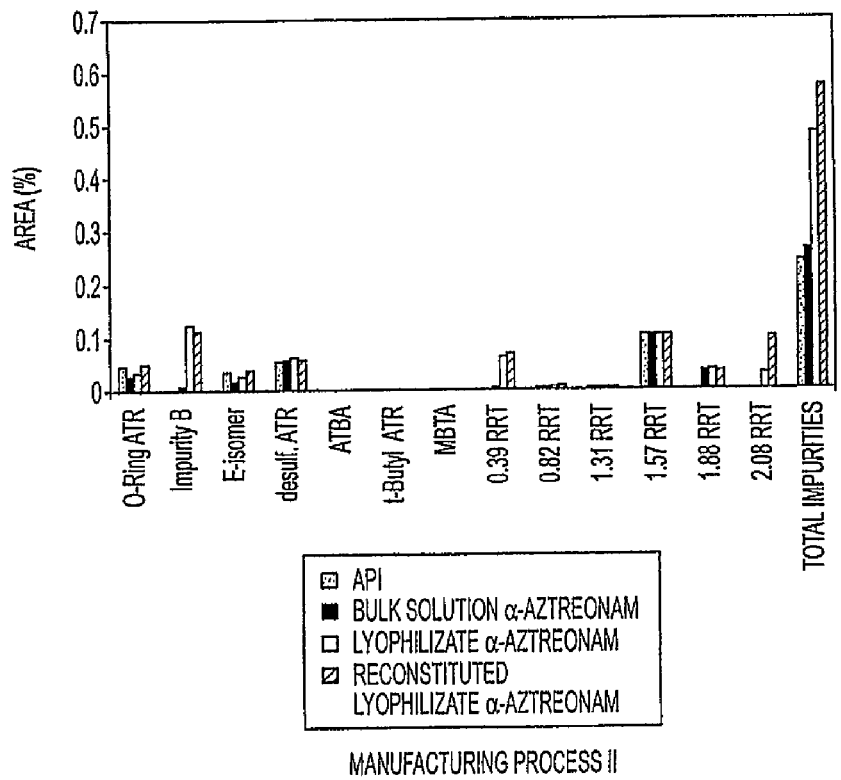

FIG. 6 graphically illustrates the impurity profiles of the bulk solution, lyophilizate and reconstituted lyophilizate of α-aztreonam lysinate compared to API.

As seen from FIG. 6, impurities profile of API, bulk solution and lyophilizate was comparable to the profiles seen in FIG. 4. Reconstituted lyophilizates has shown overall slightly but insignificantly increased level of impurities in the reconstituted lyophilizates from about 0.471% to about 0.601%.

Utility

A process for manufacturing bulk solution and lyophilized α-aztreonam lysinate is useful for preparation of inhalable aztreonam lysinate composition comprising about 75 mg/ml of aztreonam, suitable for treatment of respiratory tract infections caused by *Burkholderia cepacia, Stenotrophomonas maltophilia, Alcaligenes xylosoxidans*, and multidrug resistant *Pseudomonas aeruginosa* as well as for treatment of other pulmonary infections caused by gram-negative bacteria.

EXAMPLE 1

Preparation of α-Aztreonam Lysinate Salt

This example describes procedure used for preparation of α-aztreonam lysinate salt.

α-Aztreonam (29.4 g with 15% moisture, equivalent to 25.0 g anhydrous) was suspended and rapidly stirred in water (190 mL) and cooled on a crushed ice bath. L-Lysine (anhydrous, 17.7 g, dissolved in 40 mL of room temperature water) was titrated over 6 minutes to the milky white suspension to obtain a pH of 4.34. The total volume of the aztreonam lysinate solution was approximately 270 mL and had a yellowish color without any particulate matter. Approximately 1 g of charcoal was added to the stirring solution and was then filtered. The α-aztreonam lysinate solution was stored at a temperature of 2° C.

EXAMPLE 2

Spray Drying of α-Aztreonam Lysinate

This example describes conditions used for spray drying of α-aztreonam lysinate.

Spray drying of α-aztreonam lysinate was accomplished by spraying a fine mist of α-aztreonam lysinate solution onto a support and drying under vacuum. The dried particles are collected giving a yield of 22.2 g (56%) of α-aztreonam lysinate.

An optimized method for spray drying
Inlet Set 135° C.
Aspirator 90% (a value of 100%=35 cubic meters/hr).
Pump 34% (a value of 100%=1500 mL/hr).
Ar flow at nozzle 400 L/hr initial; at middle of run increased to 600 L/hr.
Receiver flask temp 35 to 40° C.

What is claimed is:

1. A process for manufacturing a bulk solution of a pure α-aztreonam lysinate soluble in water or aqueous solvents having an impurity level 1% or lower, said pure α-aztreonam lysinate being suitable for aerosolization and delivery by inhalation, said process comprising steps:
    (a) preparing separately a solution of:
        (i) α-aztreonam dissolved in water or an aqueous solvent at acidic pH lower than pH 6.0 to form a slurry; and
        (ii) lysine monohydrate dissolved in water or an aqueous solvent;
    wherein both α-aztreonam and lysine are present in equimolar amounts in a ratio of 1.4:1.0 of α-aztreonam to lysine monohydrate;
    (b) reacting said α-aztreonam with said lysine to produce α-aztreonam lysinate without need for conversion of α-aztreonam to β-aztreonam, wherein during said reaction said lysine solution is added to said α-aztreonam slurry or said α-aztreonam slurry is added to the lysine solution, and
    wherein said pure α-aztreonam lysinate has stability for about two years, wherein the level of impurities is 1% or lower.

2. The process of claim 1 additionally comprising step (c), purifying said α-aztreonam lysinate bulk solution until the level of impurities is 0.1% or lower.

3. The process of claim 1 additionally comprising step (d) lyophilizing the solution of step (b) into a lyophilizate having a water content between 0.3 and 0.5%.

4. The process of claim 1 wherein said step (b) is performed under continuous stirring and at a pH maintained between a value of 4.0 and 6.0.

5. The process of claim 1, further comprising purification of pure α-aztreonam lysinate bulk solution with charcoal or filtration, until the level of impurities is 0.1% or lower.

6. The process of claim 1 wherein said α-aztreonam lysinate bulk solution is vacuum or freeze dried.

7. The process of claim 1 wherein said α-aztreonam lysinate bulk solution comprises about 75 mg of α-aztreonam and about 52.5 mg of lysine monohydrate per one milliliter of water or aqueous solvent.

8. The process of claim 1 wherein said α-aztreonam lysinate bulk solution is freeze dried and has an impurity level lower than 1%.

9. The process of claim 1 wherein said pure α-aztreonam lysinate is substantially free of ethyl ester contaminant and ethyl alcohol residue.

10. The process of claim 1 wherein said α-aztreonam is combined and reacted with said lysine monohydrate is a lyophilizer.

11. The process of claim 1 wherein said α-aztreonam lysinate bult solution is spray-dried into a bulk solid α-aztreonam lysate.

12. A pure α-aztreonam lysinate suitable for inhalation treatment of pulmonary infections caused by gram-negative bacteria,
    wherein said pure α-aztreonam lysinate has levels of contaminants 1% or lower,
    wherein said pure α-aztreonam lysinate has stability, at said purity level 1% or lower, for about two years,
    wherein said α-aztreonam lysinate is dissolved in water or in an aqueous solvent into an aerosolable solution comprising 75 mg of α-aztreonam per one milliliter of the solvent, and having PH between 4.0 and 6.0, saline content from about 0.1 to about 0.90% of chloride and osmolality of from about 400 to about 550 mOsm/kg, and
    wherein said aerosolable solution is nebulized into an aerosol having a particle size with a mass medium average diameter from about 1 to about 5μ and delivered to a subject in need of said treatment.

13. The α-aztreonam lysinate of claim 12 wherein said α-aztreonam lysinate solution is lyophilized.

14. The α-aztreonam lysinate of claim 13 dissolved in from about 1 to about 5 mL of an aerosolable solution containing from about 0.1 to about 0.45% of chloride or an equivalent thereof.

15. The α-aztreonam lysinate of claim 12 lyophilized, freeze dried or vacuum dried into an inhalable dry powder and administered as the dry inhalable powder, wherein said dry powder has particle sizes predominantly between about 1 and about 5 microns and wherein said dry powder is delivered by a dry powder inhaler or by a metered dose inhaler.

16. An inhalable pharmaceutically acceptable composition comprising about 75 mg of pure α-aztreonam lysinate per one milliliter dose, said composition suitable for inhalable treatment of pulmonary bacterial infections caused by gram-negative bacteria,
    wherein said pure α-aztreonam lysinate has levels of contaminants 1% or lower,
    wherein said pure α-aztreonam lysinate has stability, at said purity level of 1% or, for about two years,
    wherein said α-aztreonam lysinate is dissolved in water or in an aqueous solvent into an aerosolable solution comprising 75 mg of α-aztreonam per one milliliter of the solvent, having pH between 4.0 and 6.0, saline content from about 0.1 to about 0.45% of chloride and osmolality of from about 400 to about 550 mOsm/kg, and
    wherein said aerosolable solution is nebulized into an aerosol having a particle size with a mass medium average diameter from about 1 to about 5 μ and is delivered to a subject in need of said treatment.

17. The composition of claim 16 wherein the α-aztreonam lysinate is spray dried into a powder having a particle size with a mass medium average diameter from about 1 to about 5μ.

18. The α-aztreonam lysinate of claim 15 wherein the α-aztreonam lysinate dry powder has total impurities of about 0.84% after 6 months of storage at 50° C.

19. The α-aztreonam lysinate of claim 15 having stability for at least two years wherein total impurities present in said α-aztreonam lysinate at two years are 1% or lower.

* * * * *

UNITED STATES PATENT AND TRADEMARK OFFICE
CERTIFICATE OF CORRECTION

| | | |
|---|---|---|
| PATENT NO. | : 7,138,419 B2 | Page 1 of 7 |
| APPLICATION NO. | : 10/882985 | |
| DATED | : November 21, 2006 | |
| INVENTOR(S) | : Alan Bruce Montgomery, Iain Duncan and Peter Carbonaro | |

It is certified that error appears in the above-identified patent and that said Letters Patent is hereby corrected as shown below:

Replace the issued informal drawings, i.e., FIG. 1 to FIG. 6, with the drawings marked as "Replacement Sheet".

At column 3, line 38, insert --,-- after "base".

At column 8, line 39, insert --monohydrate-- between "lysine" and "ratio".

At column 13, line 20, "15,812%" should read --15.812%--.

At column 13, line 21, "15,867%" should read --15.867%--.

At column 21, line 32, i.e., the 13th line of Claim1, delete "equimolar amounts in".

At column 21, line 66, i.e., the second line of Claim 10, "is" should read --in--.

At column 22, line 2, i.e., the second line of Claim 11, "bult" should read --bulk--.

At column 22, line 15, i.e., the 12th line of Claim 12, insert --sodium-- between "of" and "chloride".

At column 22, line 49, i.e., the 14th line of Claim 16, insert --sodium-- between "of" and "chloride".

Signed and Sealed this

Twentieth Day of November, 2007

JON W. DUDAS
*Director of the United States Patent and Trademark Office*